United States Patent [19]

Chubachi et al.

[11] Patent Number: 4,541,281

[45] Date of Patent: Sep. 17, 1985

[54] ULTRASONIC MICROSCOPE SYSTEM

[76] Inventors: Noriyoshi Chubachi, 4-6-203, Katahira 1-chome, Sendai-shi, Miyagi; Junichi Kushibiki, 48, Aza-Nakazaike, Arai, Sendai-shi, Miyagi, both of Japan

[21] Appl. No.: 595,865

[22] Filed: Apr. 2, 1984

[30] Foreign Application Priority Data

Apr. 3, 1983 [JP] Japan ................................. 58-58368
May 11, 1983 [JP] Japan ................................. 58-83428
Oct. 25, 1983 [JP] Japan ................................. 58-200678

[51] Int. Cl.$^4$ .......................................... G01N 29/04
[52] U.S. Cl. ........................................ 73/606; 73/602; 73/619; 73/607
[58] Field of Search ................ 73/606, 607, 618, 619, 73/602

[56] References Cited

U.S. PATENT DOCUMENTS 4,378,699 4/1983 Wickramasinghe ................... 73/606
4,491,020 1/1985 Chubachi .............................. 73/606

FOREIGN PATENT DOCUMENTS 3225586 1/1983 Fed. Rep. of Germany .......... 367/7

Primary Examiner—Howard A. Birmiel
Attorney, Agent, or Firm—Pollock, Vande Sande and Priddy

[57] ABSTRACT

An ultrasonic transmitter-receiver for radiating a focused ultrasonic beam and a sample are moved relative to each other in the axial direction of the ultrasonic beam. A reflected wave from the sample is received and a curve V(Z) of variations in the level of the reflected wave with respect to the relative movement is obtained. A reference level of interference of a directly reflected wave and a leaky elastic wave is subtracted from V(Z) to perform waveform processing. The waveform processing output is subjected to a waveform analysis, and from the analysis results, the velocity and/or the attenuation of the leaky elastic wave are calculated.

31 Claims, 32 Drawing Figures

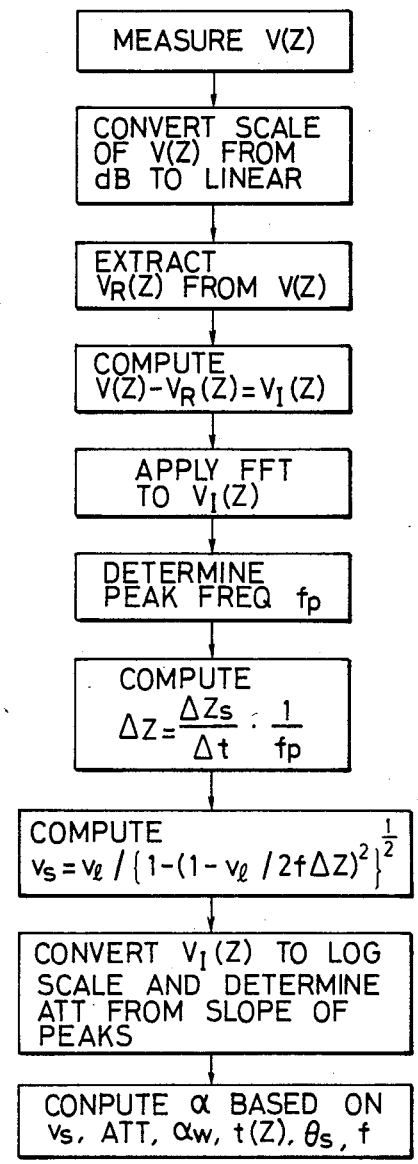

DISTANCE Z

DISTANCE Z

TIME t

TIME t

FREQUENCY f

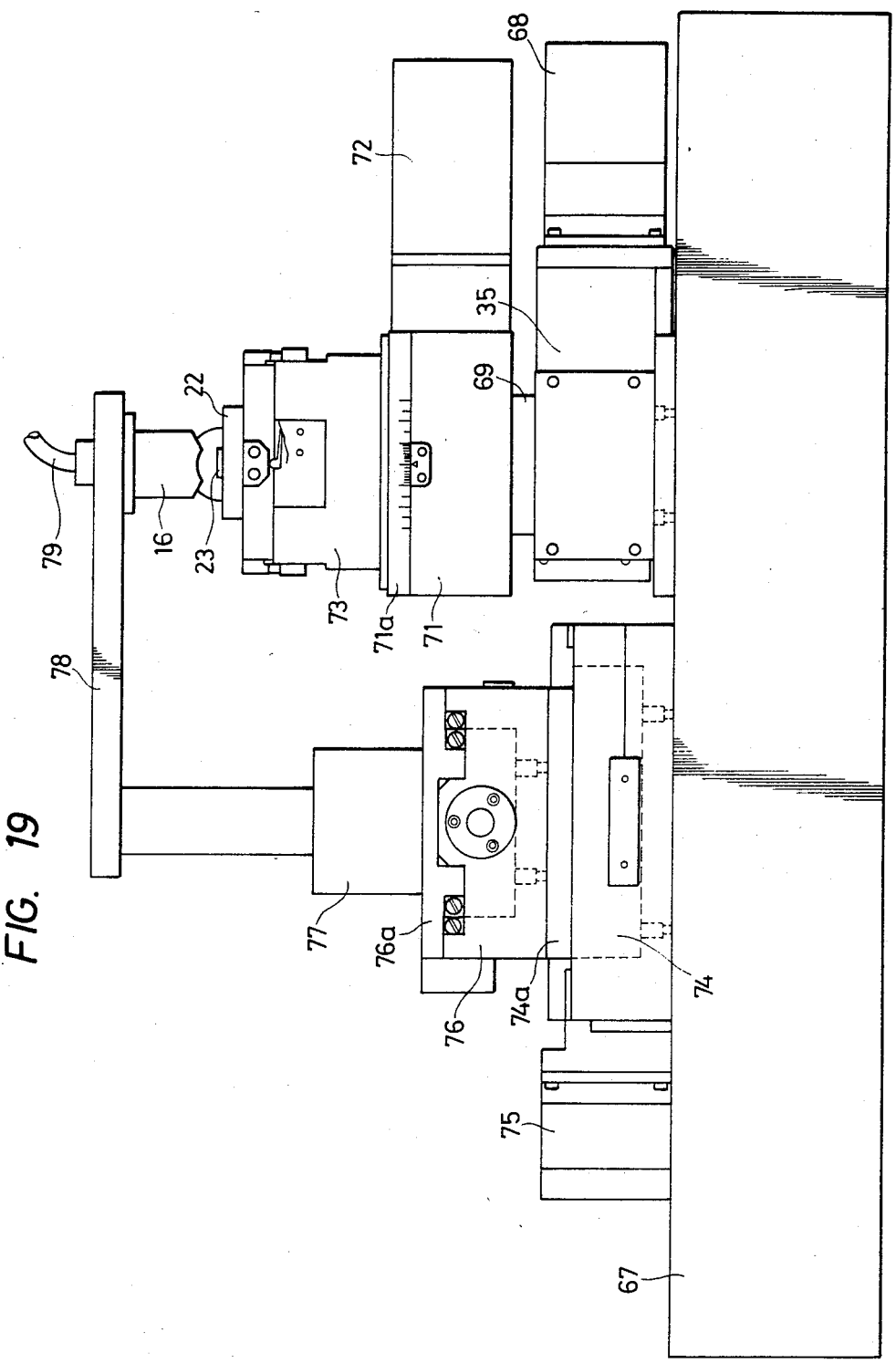

ULTRASONIC MICROSCOPE SYSTEM

BACKGROUND OF THE INVENTION

The present invention relates to an ultrasonic microscope system for measuring the acoustic characteristics of a sample through using an ultrasonic beam.

In recent years, there has been developed a mechanically scanning ultrasonic microscope for observing and measuring the microscopic or macropscopic structural and acoustic characteristics of a material through utilization of a focused ultrasonic beam, as disclosed in, for example, U.S. Pat. No. 4,028,933 issued on June 14, 1977 and "Acoustic Microscopy with Mechanical Scanning—A Review", Proceeding of the IEEE, Vol. 67, No. 8, August 1979, pp. 1092-1113. This ultrasonic microscope is, in principle, such one that applies a conically focused ultrasonic beam to a sample, moves the focal point of the beam in the plane of the sample, or in a direction perpendicular thereto, detects, by an ultrasonic transducer, reflected or transmitted waves caused by different elastic properties at respective points in the sample and converts them into electric signals for a two-dimensional display on a CRT screen to obtain an ultrasonic microscopic image, or for recording into an X-Y recorder or the like. Typical transducers for producing the focused ultrasonic beam are of the lens type and of the type in which an ultrasonic transducer is disposed on a concave or convex spherical surface. The ultrasonic microscopes are divided into the transmission type and the reflection type according to the location of the ultrasonic transducer. The abovesaid measurement is called imaging measurement by the ultrasonic microscope.

On the other hand, the abovesaid ultrasonic microscope has been modified for development of an acoustic velocity measuring apparatus. This type of apparatus is designed to observe the transducer output while moving a sample (a solid material, for example), towards the ultrasonic transducer along the beam axis (the Z-axis) instead of scanning in the X-axis and the Y-axis direction in the ultrasonic microscope. The transducer output is recorded as a periodically changing curve in a recorder. This curve is called a V(Z) curve, or an acoustic characteristic curve. It is well-known in the art that the periodicity of the V(Z) curve depends on the properties of the material to be measured and results from the interference between a reflected wave along the Z-axis of the focused ultrasonic beam directed to the sample and a reradiated wave of a leaky elastic wave excited by a beam component substantially at the critical angle. Accordingly, by measuring the dip interval $\Delta Z$ representing the periodicity of the V(Z) curve, it is possible to know the acoustic characteristics of the material. The relation between the dip interval $\Delta Z$ and velocity is given by the following equation, approximately:

$$\Delta Z = V_l / \{2f(1 - \cos \theta)\} \quad (1)$$

$$\theta_s = \sin^{-1}(V_l/V_s) \quad (2)$$

where $\theta_s$ is the critical angle, $V_l$ is the velocity of a longitudinal wave in a liquid acoustic field medium, $V_s$ is the velocity of the leaky elastic wave and f is the ultrasonic frequency used. Therefore, according to this acoustic velocity measuring apparatus, by measuring the interval $\Delta Z$, the velocity of the leaky elastic wave $V_s$ can be obtained from the following equation:

$$V_s = V_l / \{1 - (1 - V_l/2f\Delta Z)^2\}^{\frac{1}{2}} \quad (3)$$

An example of this is disclosed in Weglein, "A Model for Predicting Acoustic Material Signatures". Applied Physics Letters, Feb. 1, 1979. Vol. 34, No. 3, pp. 179-181, and this article experimentally clarifies that this method is useful for the quantitative measurement of the acoustic characteristics of solids. This measurement is called quantitative measurement of the acoustic measurement of a sample by the ultrasonic microscope.

For the velocity determination by this measurement, it is necessary that the dip intervals $\Delta Z$ in the V(Z) curve appear regularly. In general, however, the situation often arises where the dip intervals $\Delta Z$ and the waveform of the V(Z) curve are so irregular that the dip intervals $\Delta Z$ cannot be obtained from the curve, making it difficult to measure the velocity $V_s$ of the leaky elastic wave from the V(Z) curve.

The V(Z) curve recorded by the ultrasonic microscope apparatus includes every elastic information of the sample, and the abovesaid velocity measurement is an extraction of a part of the information. The V(Z) curve also includes an important factor which greatly affects the shape of an interference amplitude, that is, the propagation attenuation of the leaky elastic wave which contributes to the interference. It is considered that the amplitude attenuation of a leaky elastic wave which propagates on the boundary between the liquid acoustic field medium and the sample in the ultrasonic microscope apparatus is mainly caused by such three effects as (i) the radiation of the acoustic wave energy into the liquid owing to the acoustic loading of the liquid on the sample, (ii) the acoustic absorption by the sample and (iii) the scattering of acoustic waves due to the surface roughness of the sample and by the structural factors in the sample, such as cracks, pores and grain boundaries in the sample in which the leaky wave energy is distributed. Accordingly, by measuring the propagation attenuation of one or more leaky elastic waves which contribute to the V(Z) curve, it is possible to detect the acoustic impedance, the surface state and the internal structure of the sample.

In order to determine the propagation attenuation of the leaky elastic waves, two methods have been proposed and employed so far for the V(Z) curve obtained with the use of a conically focused ultrasonic beam. One of the methods is to estimate the attenuation by comparing the depths of dips or the magnitude of the interference amplitude in the measured V(Z) curve with those of the V(Z) curve obtained by theoretical calculations. The other method is to directly measure the attenuation of the leaky elastic wave amplitude, eliminating the response of the ultrasonic transducer to the ultrasonic beam component near the center axis of the beam in the V(Z) curve by attaching a sound absorber to an acoustic lens centrally thereof, using specially designed electrodes of the transducer, or employing an acoustic field suitable for the measurement so as to remove the beam component along the center axis of the beam, as described in, for instance, Smith et al., "SAW Attenuation Measurement in the Acoustic Microscope", ibid., 1982, 18, pp. 955-956.

However, these measuring methods have such fatal defects as follows: That is, the former method consumes much time for the comparison of the measured values with the calculated ones and insufficient in the correspondence between them because of the approximation by theoretical calculations, and hence is unsatisfactory in measurement accuracy. The latter method is inconvenient in that the velocity of the elastic wave must be measured using other methods such as the ordinary V(Z) curve method because the wave velocity is needed to determine the wave attenuation.

SUMMARY OF THE INVENTION

It is therefore an object of the present invention to provide an ultrasonic microscope apparatus which permits accurate measurement of the dip intervals ΔZ even if the dip intervals ΔZ and the shape of the V(Z) curve have irregularities, and which, therefore, ensures accurate measurement of the velocity of a leaky elastic wave in a sample.

Another object of the present invention is to provide an ultrasonic microscope apparatus which permits simultaneous measurement of the velocity and attenuation coefficient of a leaky elastic wave in a sample from the V(Z) curve.

Yet another object of the present invention is to provide an ultrasonic microscope apparatus which is capable of quantitative measurement of each part of a sample subjected to imaging measurement.

According to the ultrasonic microscope of the present invention, high-frequency pulses from a high-frequency pulse generator are supplied to an ultrasonic transmitter-receiver, from which they are each radiated as an ultrasonic beam to a sample. A reflected wave from the sample is converted by the ultrasonic transmitter-receiver into an electric signal, which is amplified and rectified by a detector circuit. The radiation of the ultrasonic wave and the reception of the reflected wave take place while changing the distance between the ultrasonic transmitter-receiver and the sample along the beam axis by Z-axis moving means. Each time the distance between the ultrasonic transmitter-receiver and the sample is changed by a fixed value, the reflected signal output is picked up from the detector circuit, thus obtaining a V(Z) signal indicating the reflected signal levels in relation with distances between the ultrasonic transmitter-receiver and the sample. The V(Z) signal is subjected to a waveform analysis by waveform analyzing means using the spectral analysis techniques, such as an FFT method, frequency analysis method using a filter, or maximum entropy method, thereby obtaining the dip intervals ΔZ representing the periodicity of interference between a directly reflected wave and a leaky elastic wave from the sample.

Prior to the abovesaid waveform analysis, the reflected signal output from the detector circuit is subjected to waveform processing by waveform processing means to pick up the leaky elastic wave component, which is waveform-analyzed. Further, the attenuation of the picked-up leaky elastic wave component is calculated by attenuation calculating means, and this calculation utilizes the velocity of the leaky elastic wave based on the dip intervals ΔZ which is obtained by the waveform analysis.

The waveform processing is effected by subtracting, from the reflected wave signal, a reference signal indicating the reference level of the interference between the reflected wave and the leaky elastic wave. The attenuation coefficient of the leaky elastic wave component is obtained by the attenuation calculating means from the gradient of a line joining the peaks of the waveform of the leaky elastic wave component.

Further, the ultrasonic transmitter-receiver and the sample are moved by XY driver means relative to each other in a plane perpendicular to the beam axis to perform two-dimensional scanning of the sample by the ultrasonic beam. A reflected or transmitted wave from the sample during the two-dimensional scanning thereof is converted into an electric signal, which is amplified and rectified, and its level is image-displayed corresponding to each two-dimensional scanning position. The velocity and/or attenuation of the leaky elastic wave are displayed as an image, or in a numeric form, corresponding to each position of the image display. Moreover, the ultrasonic transmitter-receiver and the sample are oscillated at right angles to the beam axis at a speed sufficiently higher than the speed of their movement along the beam axis, by which mean velocity and attenuation of the leaky elastic wave for a certain region of the sample are measured.

BRIEF DESCRIPTION OF THE DRAWINGS

FIG. 13 is a flowchart illustrating an example of the operation of measuring velocity $V_s$ and attenuation coefficient $\alpha_s$;

FIG. 19 is a front view showing the outline of the external appearance of the ultrasonic microscope apparatus of the present invention.

DESCRIPTION OF THE PREFERRED EMBODIMENTS

Figure 1:
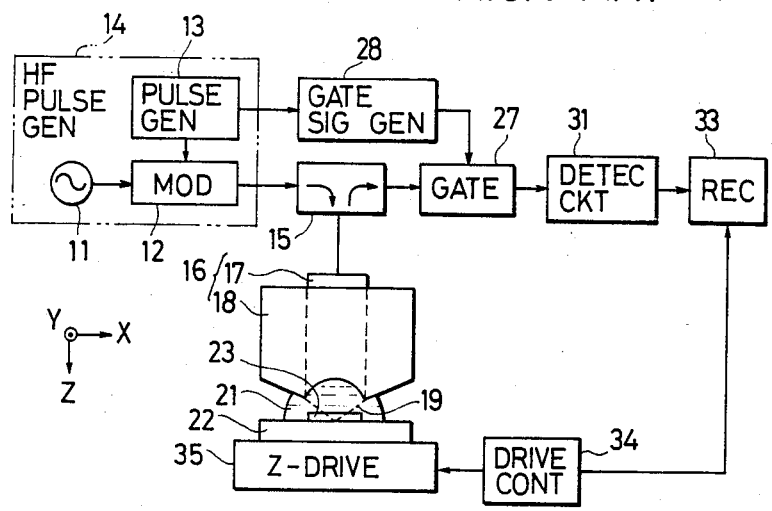
FIG. 1 is a block diagram illustrating a conventional ultrasonic microscope apparatus which performs quantitative measurement.

To facilitate a better understanding of the present invention, a description will be given, with reference to FIG. 1, of a conventional ultrasonic microscope apparatus for measuring the velocity of leaky elastic waves in a sample material. A sine-wave signal of an ultrasonic frequency is supplied from a signal source 11 to a modulator 12, wherein it is pulse-modulated by pulses from a pulse generator 13 into a high-frequency pulse signal. The signal source 11, the modulator 12 and the pulse generator 13 constitute a high-frequency pulse generator 14. The high-frequency pulse signal from the high-frequency pulse generator 14 is provided via a duplexer 15, such as a circulator, directional coupler or the like, to a transducer 17 of an ultrasonic transmitter-receiver 16 for conversion into an ultrasonic pulse. The ultrasonic pulse is emitted, as an ultrasonic point-focus beam 19 conically focused by an acoustic lens 18 as of sapphire, into a liquid acoustic field medium 21.

Figure 2A:
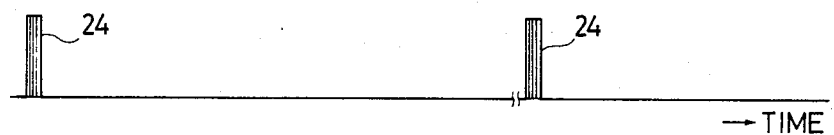
FIGS. 2A to 2E show a timing chart for assistance in explaining the operation of the apparatus shown in FIG. 1.
Figure 2B:
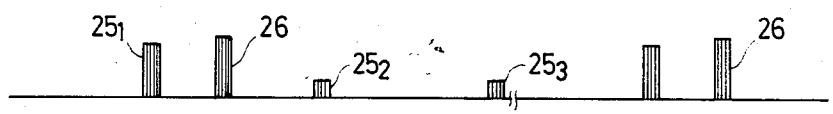
Figure 2C:
Figure 2D:
Figure 2E:

A sample 23 is mounted on a sample holder 22 in the vicinity of the focal point of the acoustic lens 18 in the liquid acoustic field medium 21 and is irradiated by the ultrasonic beam 19. Each high-frequency pulse signal is converted by the transducer 17 into an ultrasonic pulse 24, as shown in FIG. 2A, and a portion of the energy of the ultrasonic pulse is reflected at the boundary between the acoustic lens 18 and the liquid acoustic field medium 21 to become a pulse which is repeatedly reflected between above mentioned boundary and the boundary between the transducer 17 and the acoustic lens 18 while being gradually attenuated, as indicated by $25_1$, $25_2$, $25_3$ ... in FIG. 2B. The remaining part of the energy of the ultrasonic pulse 24 passes into the liquid acoustic field medium 21 and is reflected, by the sample 23, as a reflected pulse 26, back to the transducer 17. The reflected wave is converted by the transducer 17 into an electric signal, which is provided via the duplexer 15 to a gate 27. The pulse signal from the pulse generator 13 is applied to a gate signal generator 28, and by a gate signal 29 (FIG. 2C) produced in the gate signal generator 28, the gate 27 is controlled to pass therethrough the reflected pulse 26 from the sample 23 as shown in FIG. 2D. The reflected pulse 26 is amplified and rectified by a detector circuit 31 to obtain a reflection signal 32, as shown in FIG. 2E, which is supplied to a recorder 33.

A drive controller 34 controls a Z-direction driver 35, by which the sample holder 22 is moved towards the transmitter-receiver 16 along the axis (Z-axis) of the ultrasonic beam 19. A signal corresponding to the distance of movement of the sample holder 22 in the Z-direction is provided from the drive controller 34 to the recorder 33, recording therein the varying states of the level of the reflection signal 32 which are caused by changes in the distance Z between the transmitter-receiver 16 and the sample 23.

Let it be assumed that leaky elastic surface waves exist, as a leaky elastic wave mode, at the boundary between the liquid acoustic field medium 21 and the sample 23. In such a case, as illustrated on an enlarged scale in FIG. 3, there are effectively a component of a directly reflected wave 36 which is incident on the sample 23 substantially along the center axis of the acoustic lens 18 and reflected by the sample 23 back to the transducer 17, and a component of a leaky elastic wave 37 which is incident on the sample 23 at a leaky elastic surface wave critical angle $\theta_s$ and propagates a certain distance on the surface of the sample 23, thereafter being reradiated into the liquid acoustic field medium 21 and back to the ultrasonic transducer 17. Such a V(Z) curve as shown in FIG. 4, which has periodic dips 38 in the output level waveform of the detector circuit 31 owing to the interference of these two components, is recorded into the recorder 33. By measuring the dip interval $\Delta Z$, the velocity $V_s$ of the leaky elastic surface wave in the sample 23 can be obtained from Eq. (3) mentioned previously. In FIG. 4, when Z=0 the sample 23 lies at the focal point of the acoustic lens 18, and as the sample 23 approaches the transmitter-receiver 16, the distance Z increases in one direction.

In the velocity measurement based on the V(Z) curve, the use of the point-focus ultrasonic beam has the advantage that an acoustic characteristic for a minute portion of the sample can be detected, but due to the symmetrical configuration of the beam, its energy spreads in all directions around the beam axis, so that when the sample 23 has antisotropy about the Z-axis, anisotropy dependent upon the wave propagation direction cannot be detected, and the velocity is measured as a mean value. For quantitatively precise measurement including anisotropy, an ultrasonic microscope which uses a linearly focused ultrasonic beam (line-focus beam) has been proposed in U.S. patent application Ser. No. 6/395,711 filed on July 6, 1982 and IEEE Ultrasonics Symp. Proc., pp. 552–556 (1981).

Figure 5:
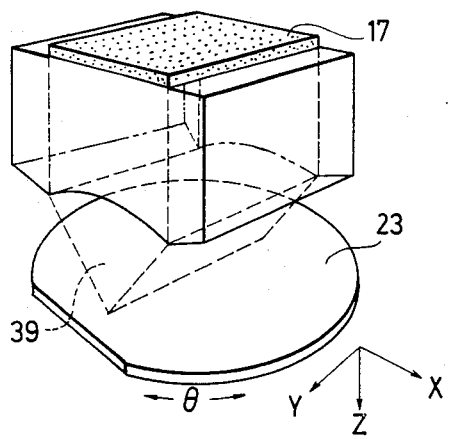
FIG. 5 is a perspective view illustrating an example of an ultrasonic line-focus beam.

FIG. 5 schematically illustrates a method for detecting acoustic anisotropy of a solid material about the Z-axis through using the ultrasonic line-focus beam. An ultrasonic line-focus beam 39 is applied to the sample 23 through the liquid acoustic field medium (not shown in FIG. 5), and the V(Z) curve is recorded while moving the sample 23 in the Z-axis direction in the same manner as in the case of using the aforesaid ultrasonic point-focus beam 19. The relation between the dip interval $\Delta Z$ and the velocity of leaky elastic waves in the solid is exactly the same as described previously in the case of using the ultrasonic point-focus beam 19. Since the leaky elastic waves can be excited only in a direction perpendicular to the focused line of the ultrasonic beam 39, i.e. in the X-direction, the propagation velocity in the X-direction can be measured. By repeating such measurement while turning the sample 23 about the Z-axis by steps of a predetermined small angle, the anisotropy of the sample 23 around the Z-axis can be measured as a difference in velocity value of the leaky elastic waves. That is, when using the ultrasonic line-focus beam 39, the anisotropy of a crystal can be expressed by the relation between the rotated angle $\theta$ and the velocity.

For determining the velocity by such a measurement method as mentioned above, it is necessary that the dips in the V(Z) curve appear at regular intervals. In many cases, however, the V(Z) curves generally observed are appreciably irregular in dip interval and in shape, as shown in an experimental example of FIG. 6. This phenomenon often occurs in cases of a sample having anisotropy or a layered structure (including a diffusion layered structure) and a sample not so large in thickness as compared with the wavelength of the ultrasonic waves used. As the cause of this phenomenon, it was considered that a plurality of leaky elastic wave modes generally exist in such samples and complicated interferences of reflected waves of the respective modes would disturb the dip interval and the shape of the V(Z) curve. It has been proved, as a result of our various experiments and studies, that the complex V(D) curve results from the superposition of V(Z) curves obtainable on the assumption that waves of respective modes exist simultaneously and independently.

Figure 7:
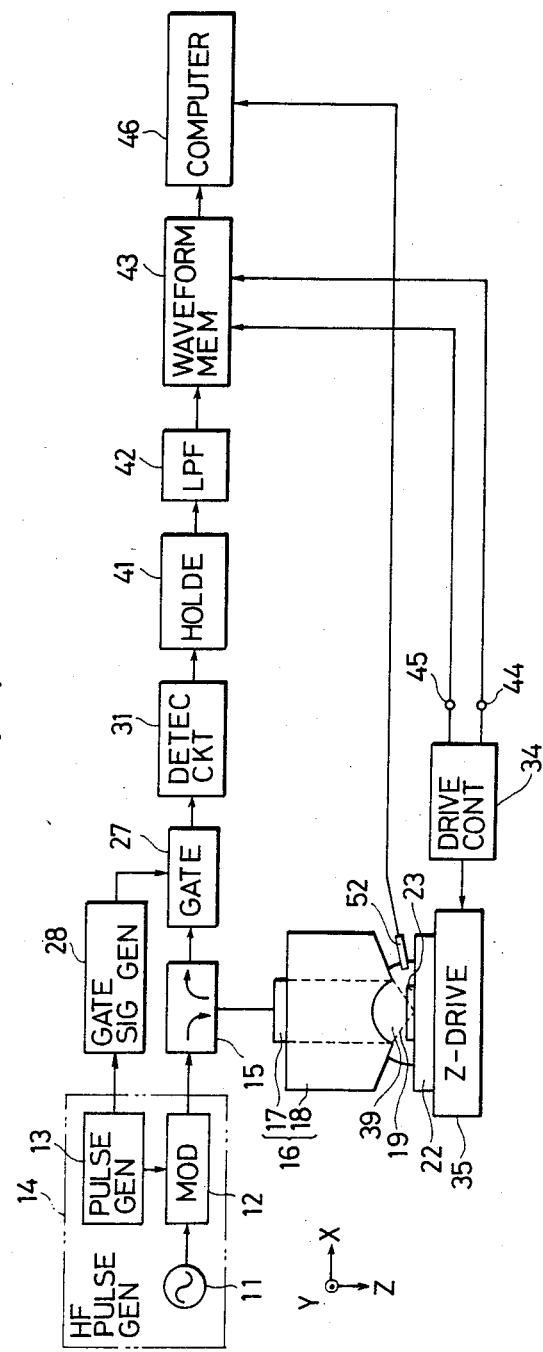
FIG. 7 is a block diagram illustrating an embodiment of the ultrasonic microscope apparatus of the present invention which is equipped with the quantitative measurement function.

FIG. 7 illustrates a block diagram of an embodiment according to the present invention, in which the parts corresponding to those in FIG. 1 are identified by the same reference numerals. The transmitter-receiver 16 used in this embodiment is such one that is capable of producing the line-focus ultrasonic beam 39. It is also possible to employ the transmitter-receiver of the type producing the point-focus ultrasonic beam. The reflected signal output of the detector circuit 31 is provided to a holding circuit 41, such as a peak holder or sampling holder, in which the peak (or sample) value of each reflected signal pulse is held, and the output of the holding circuit 41 has its noise component removed by a low-pass filter 42, thereafter being supplied to a waveform memory 43. By controlling the Z-axis driver 35 from the drive controller 34, for example, by applying 500 Hz pulses to a step motor, the sample 23 is moved towards the transmitter-receiver 16 by steps of a certain value, for instance, 0.1 μm. The pulse repetition frequency of the pulse generator 13 is set to, for example, 10 KHz. A trigger pulse, which indicates the start of this operation, is applied from a terminal 44 of the drive controller 34 to the waveform memory 43 to put it in operation. Clock pulses are provided to the waveform memory 43 from a terminal 45 of the drive controller 34 and, for each upward movement of the sample 23, the output of the filter 42 is sampled, and the sample value is specified by an address generated in the waveform memory 43 and stored therein, for instance, as a 12-bit digital value. The address is altered for each step of the upward movement of the sample 23. When the sample 23 has been moved towards the transmitter-receiver 16 by a predetermined number of steps, for example, 8192, the data stored in the waveform memory 43 are transferred to an electronic computer (a data processor) 46. The movement of the sample 23 is effected to such an extent as to provide at least three dips in the V(Z) curve. The data thus transferred to the electronic computer 46, that is, the data representing the V(Z) curve, are subject to an FFT analysis in accordance with an algorithm generally employed.

Figure 8:
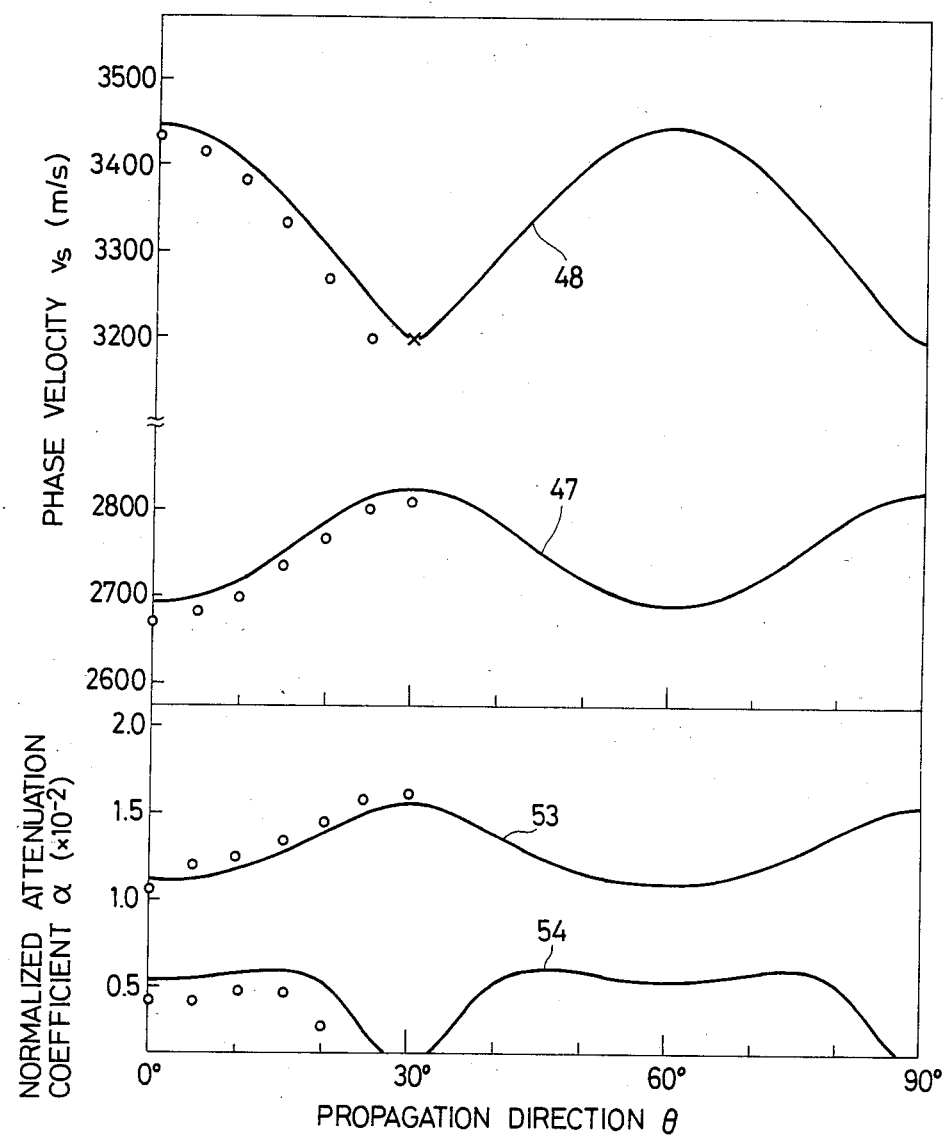
FIG. 8 is a graph showing theoretical and experimental values of the phase velocity $V_s$ and the normalized attenuation coefficient $\alpha_s$ of a leaky elastic surface wave and a leaky pseudo-elastic surface wave on a (111)-Ge sample in a propagation direction $\theta$.

A description will be given of the results of experiments conducted on a (111)-Ge (belonging to crystal system m3m) through the use of the apparatus illustrated in FIG. 7. Water is used as the liquid acoustic field medium 21. As leaky elastic waves which exist and propagate on the boundary between the water 21 and the (111)-Ge sample 23, there are two leaky modes of waves, i.e. a leaky elastic surface wave and a leaky pseudo-elastic surface wave which propagate while slightly radiating its acoustic energy into the (111)-Ge sample 23, too. FIG. 8 shows the dependency of the leaky elastic wave velocity on the propagation direction ($\theta$) resulted from the anisotropy of the (111)-Ge sample 23 around the Z-axis. The curve 47 indicates the propagation characteristic of the leaky elastic surface wave and the curve 48 the propagation characteristic of the leaky pseudo-elastic surface wave. In this case, it is indicated that the anisotropy is dependent on the crystalline symmetry of the sample 23 and that the characteristics in all directions are determined by the relationship between the angle $\theta$ from 0° to 30° and the acoustic velocity. As regards acoustic wave propagation in the direction of $\theta = 30°$ and in symmetrical angular directions thereof, there does not exist the leaky pseudo-elastic surface wave, theoretically, except a leaky pure Rayleigh wave.

Figure 6:
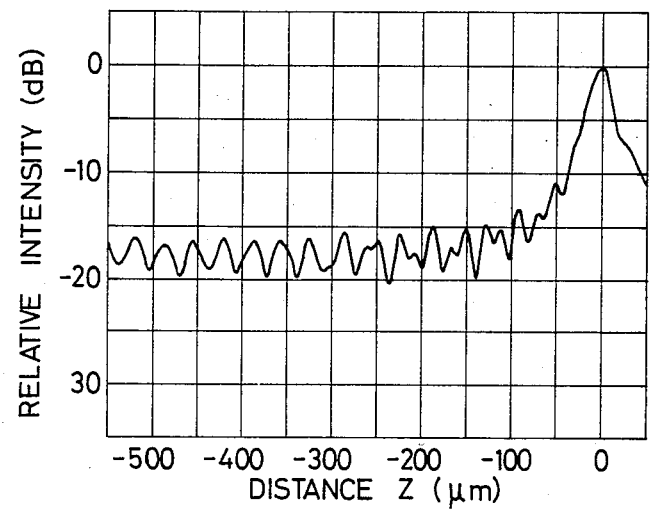
FIG. 6 is a graph showing an example of the V(Z) curve of an irregular shape.
Figure 9:
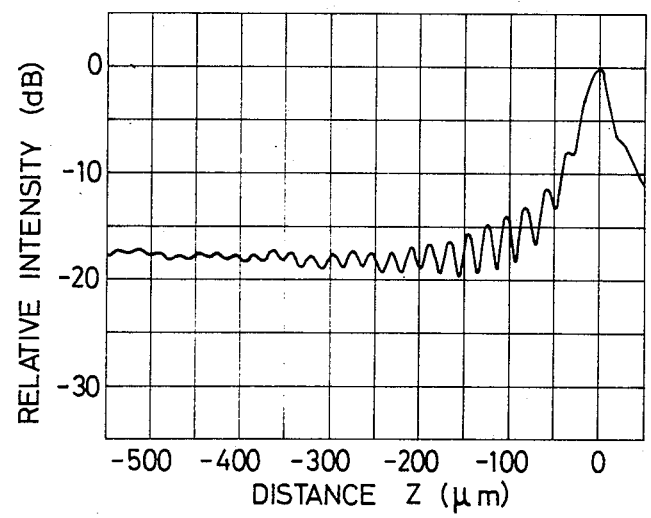
FIG. 9 is a graph showing the V(Z) curve for the (111)-Ge sample in a direction $\theta = 30°$.
Figure 10:
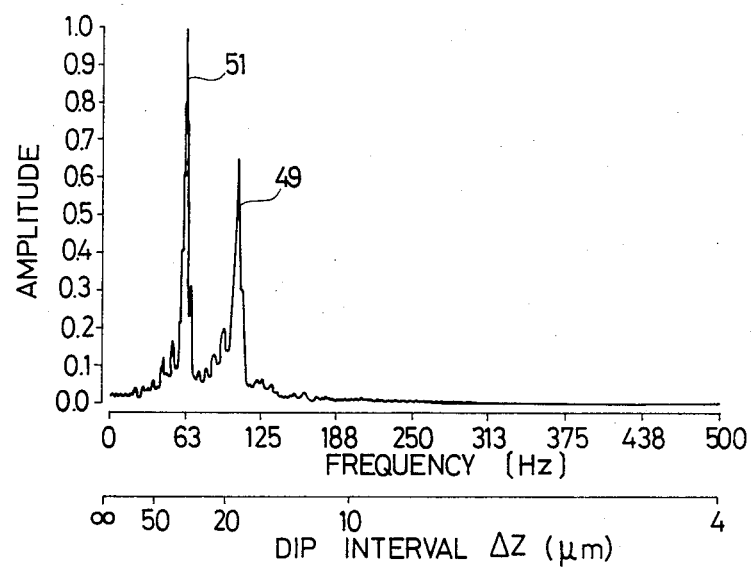
FIG. 10 is a graph showing the FFT-analyzed spectrum of an interference wave in the V(Z) curve depicted in FIG. 6.
Figure 11:
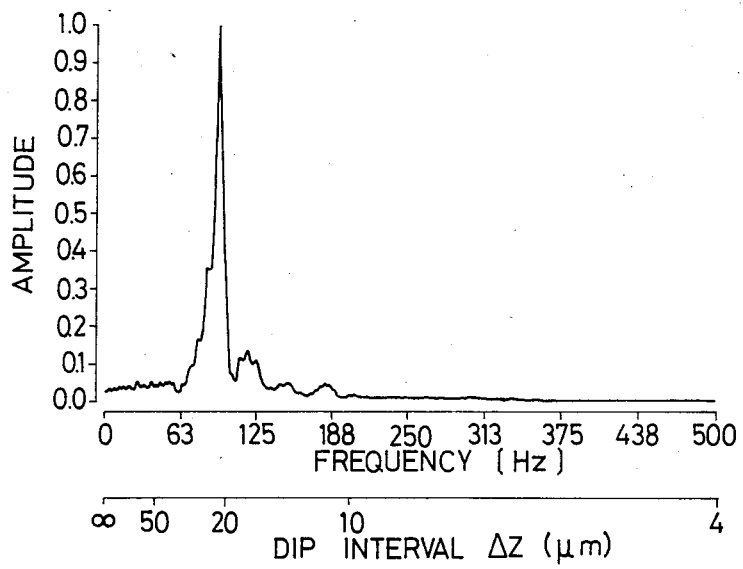
FIG. 11 is a graph showing the FFT-analyzed spectrum of an interference wave in the V(Z) curve depicted in FIG. 9.

Now, the FFT waveform analysis is applied, by the electronic computer 46, to V(Z) curves obtained for the directions of $\theta = 0°$ and $\theta = 30°$ with respect to the (111)-Ge sample in the case of the ultrasonic frequency used for measurement being 226.3 MHz. FIGS. 6 and 9 show the V(Z) curves obtained for $\theta = 0°$ and $\theta = 30°$, respectively. In the case of the V(Z) curve for $\theta = 0°$, owing to the presence of the two leaky elastic wave modes, the waveform is more deformed, as shown in FIG. 6, than in the case of the V(Z) curve for the direction $\theta = 30°$ (FIG. 9) in which only one leaky elastic wave mode exists, and it is easily seen that it is difficult to employ the conventional velocity measurement method described previously with regard to FIG. 1. FIGS. 10 and 11 show the results of the FFT analysis of the two Z(V) curves. In this case, the two V(Z) curves were analyzed, by FFT, after extracting therefrom a $V_R(Z)$ curve (described later) indicating a reference level of interference between the reflected wave (the directly reflected wave) along the center axis and the leaky elastic wave. The FFT analysis was applied to sample data of 8192 sample points in total, 551 points of which were obtained from the waveform of each of the V(Z) curves shown in FIGS. 6 and 9, the remaining points having been added as dummy points to the front and rear of the 551 sample points so as to obtain a sufficiently high velocity resolution for the leaky elastic wave. In FIG. 10 maximal spectra appear at a peak frequency 49 of fp(LSAW)=51.64 Hz for the leaky elastic surface wave and at a peak frequency 51 of fp(LPSAW)=30.03 Hz for the leaky pueudo-elastic surface wave, respectively. By using the relation expressed by the following equation, the dip intervals $\Delta Z$ for the respective modes can be obtained from the abovesaid frequencies:

$$\Delta Z = (\Delta Z_s / \Delta t) \cdot (1/fp) \quad (4)$$

Here, sampling distance interval $\Delta Z_s$ for the V(Z) curve is 1 μm and the sampling time interval $\Delta t$ defined when the distance variable Z is scale-converted into the time variable t is 0.001 sec. Using Eq. (3) expressing the relationship between the dip interval $\Delta Z$ and the sound velocity Vl, velocities of the leaky elastic surface wave and the leaky pseudo-elastic surface wave are calculated as Vs(LSAW)×2670 m/s and Vs(LPSAW)=3435 m/s, respectively. On the other hand, for $\theta = 30°$, the frequency at which a maximal spectrum appears for the pure leaky Rayleigh wave is $fp(LSAW)=46.14$ Hz, and the velocity can be determined as $Vs(LSAW)=2810$ m/s.

As described above, according to the present invention, even if there are irregularities in the waveform of the V(Z) curve, it is possible to separate a plurality of leaky elastic wave modes which contribute to the Z(V) curve and to measure the acoustic characteristic for each mode. Incidentally, since the sound velocity Vl in the liquid acoustic field medium 21 varies with temperature, a temperature sensor 52 is disposed in the liquid acoustic field medium 21 to detect its temperature as shown in FIG. 7, the detected value is input into the electronic computer 46, and by referring to a table showing the relation between temperature and the sound velocity Vl, the sound velocity Vl at a predetermined reference temperature is obtained for computation of the velocity Vs.

Our various experiments and researches have revealed that the V(Z) curve shown in FIG. 4 is superposition of the interference wave between the reflected wave (the directly reflected wave) along the center axis and the leaky elastic wave, and a reference signal curve $V_R(Z)$ indicating the reference level of the interference. The reference signal curve $V_R(Z)$ indicates variations in the receiving level of the reflected wave which are caused mainly by the approach of the sample 23 to the transmitter-receiver 16 from the focal point, and it is maximal near the focal point i.e., at $Z=0$. The reference signal curve $V_R(Z)$ is determined by the configurations and the operating frequencies of the transducer 17 and the line-focus acoustic lens 18. A curve obtained by extracting the reference signal curve $V_R(Z)$ from the measured V(Z) curve has the dip interval $\Delta Z$ corresponding to the leaky elastic surface wave velocity and than be expressed as an interference output waveform $V_I(Z)$ of a sine wave which attenuates in relation to the propagation length of the leaky elastic surface wave. Accordingly, the output V(Z) can be expressed approximately by the following equation:

$$V(Z) \cong V_I(Z) + V_R(Z)$$

Figure 3:
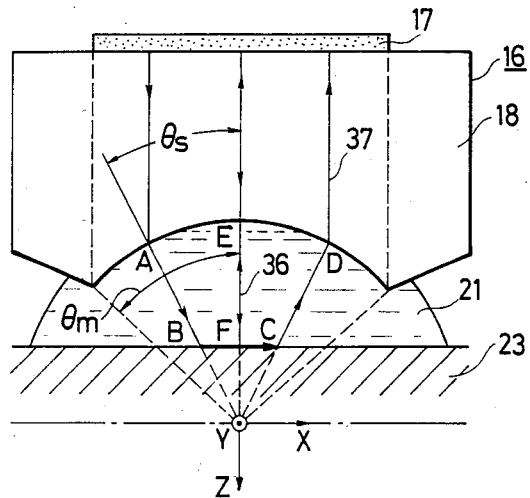
FIG. 3 shows, in section, a transmitter-receiver and a sample for assistance in explaining the interference between a directly reflected wave and a leaky elastic wave.
Figure 4:
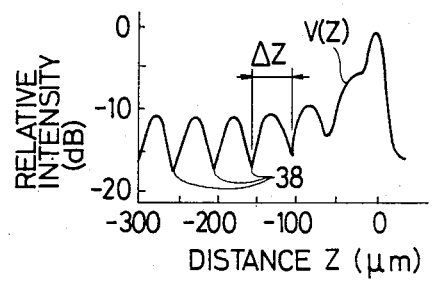
FIG. 4 is a graph showing an example of the V(Z) curve indicating variations in the level of a reflected wave with respect to the distance between the transmitter-receiver and the sample.

Here, $$V_I(Z) = C \cdot ATT \cdot \sin(\xi|Z| + \phi) \quad (5)$$

$$ATT = \exp(-2\alpha_\omega t(Z)) \cdot \exp(-1\,\gamma|Z|\tan\theta s) \quad (6)$$

$$\gamma = 2\pi f \alpha_s / V_s \quad (7)$$

$$t(Z) = \overline{AB} = \overline{CD}$$

where $\xi$ is the relative phase difference per unit propagation length between a reflected wave component 36 along the center axis and a leaky elastic surface wave component 37 in FIG. 3, $\phi$ is an initial phase difference between the components 36 and 37 at the focal plane $Z=0$, C is an arbitrary constant, f is an ultrasonic frequency, $\alpha_\omega$ is an attenuation coefficient of a longitudinal wave in the liquid sound field medium 21, Vs is the phase velocity of the leaky elastic surface wave, $\alpha_s$ is a normalized propagation attenuation coefficient of the leaky elastic surface wave, $\overline{AB}$ is the distance from the acoustic lens 18 to the point of incidence on the sample 23 at a critical angle $\theta s$ and $\overline{CD}$ is the path length of the leaky elastic surface wave from the sample 23 to the acoustic lens 18. According to the present invention, when the acoustic characteristics (the velocity and the attenuation coefficient) of the liquid sound field medium 21 are preknown, the velocity Vs of the leaky elastic wave is determined from the periodicity of the interference waveform output $V_I(Z)$ which is experimentally extracted from the acoustic characteristic, and the propagation attenuation coefficient $\alpha$ is determined from the gradient ATT of the attenuation of the interference waveform.

The hardware arrangement therefor may be the same as shown in FIG. 7. In this case, however, the attenuation of the leaky elastic surface wave is also measured by the processing in the electronic computer 46. A description will be given of the procedure for measuring the velocity Va and attenuation at the same time.

Figure 12A:
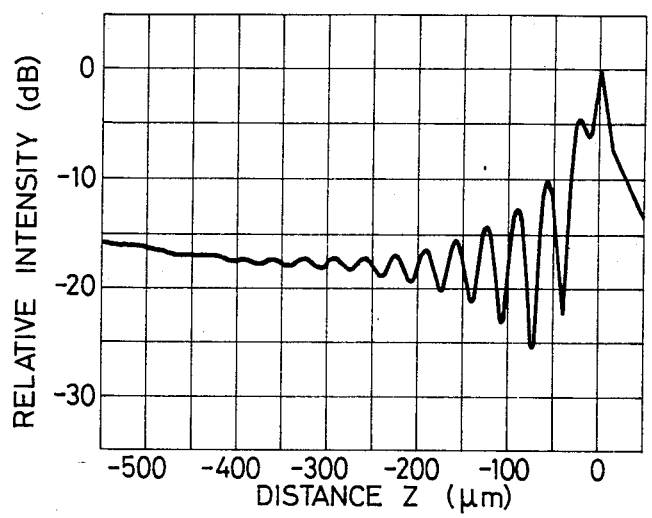
FIGS. 12A to 12F are graphs showing the steps involved in waveform processing.

(a) The V(Z) curve is measured in the same manner as in the case of velocity measurement (measurement of the dip interval $\Delta Z$), and the regulating V(Z) curve data such, for example, as shown in FIG. 12A is stored in the waveform memory 43 in FIG. 7.

Figure 12B:
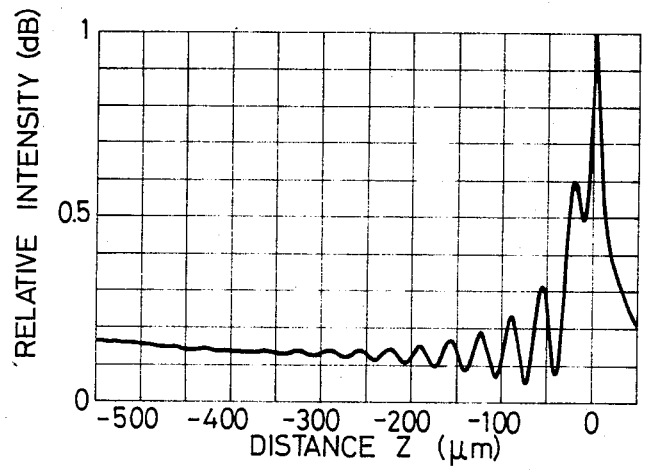

(b) The V(Z) curve data in the waveform memory 43 is input into the electronic computer 46, wherein its relative level on the ordinate is converted from a decibel scale to a linear scale to obtain V(Z) curve data shown in FIG. 12B.

Figure 12C:
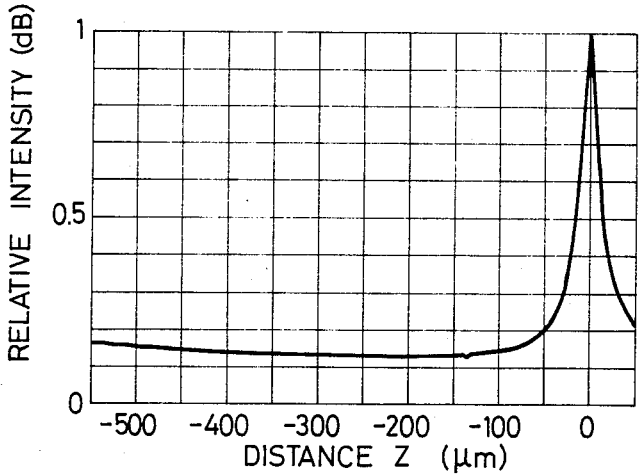

(c) The reference signal curve $V_R(Z)$ is synthesized by extraction from the V(Z) curve data through using the digital filtering techniques. That is, the V(Z) curve data is applied to a digital low-pass filter to obtain the reference signal curve data $V_R(Z)$ shown in FIG. 12C. The $V_R(Z)$ curve data may also be obtained by applying analog V(Z) curve data to an analog low-pass filter. Alternatively, the V(Z) curve data is subjected to the FFT analysis to remove its high-frequency spectral component and the remaining low-frequency spectral component is waveform-synthesized, obtaining the V(Z) curve data.

Figure 12D:
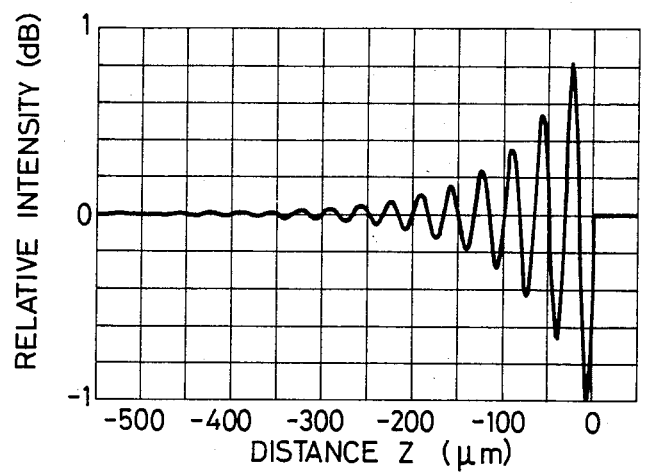

(d) The reference signal curve data $V_R(Z)$ is subtracted from the V(Z) curve data to extract the interference waveform ($V_I(Z)$), as shown in FIG. 12D.

(e) The interference waveform $V_I(Z)$ is subjected to fast Fourier transform to obtain its peak frequency fp.

(f) The dip interval $\Delta Z$ is obtained from Eq. (4) through using the peak frequency fp, and the velocity Vs of the leaky elastic surface wave is obtained from Eq. (3) through using the dip interval $\Delta Z$.

Figure 12E:
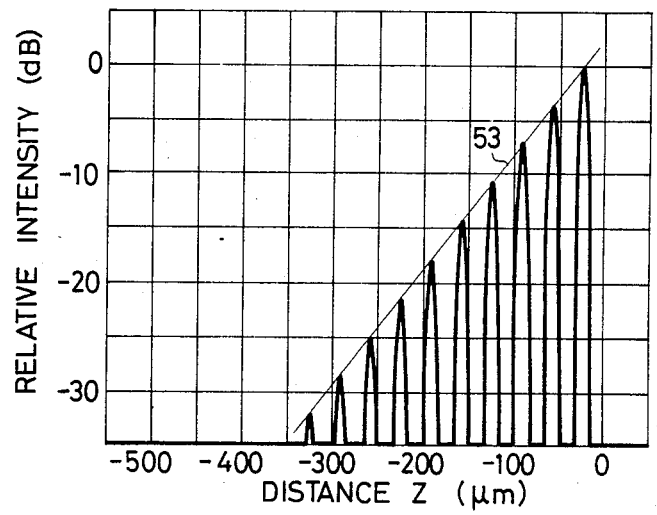

(g) The scale of the interference waveform $V_I(Z)$ on the ordinate in FIG. 12D is converted into a common logarithm to obtain such an interference waveform $V_I(Z)$ as shown in FIG. 12E. The attenuation AAT is obtained from the gradient of a line 53 joining the peaks of the waveform shown in FIG. 12E.

(h) The normalized attenuation coefficient $\alpha$ of the sample is computed from Eqs. (6) and (7) through using $\alpha_\omega$, t(Z), $\theta s$ and f which are preknown, along with Vs obtained in (f) and ATT obtained in (g).

The procedure described above is illustrated in FIG. 13.

Figure 14A:
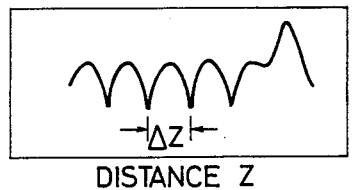
FIGS. 14A to 14E are diagrams showing the procedure of measuring the dip intervals ΔZ, using the FFT analysis.
Figure 14B:
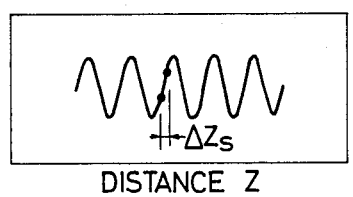
Figure 14C:
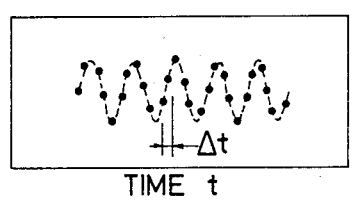
Figure 14D:
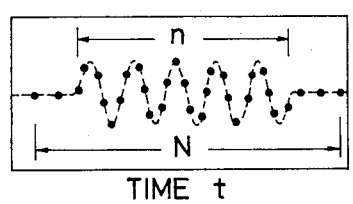
Figure 14E:
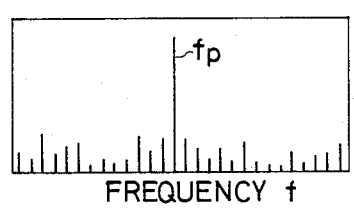

FIGS. 14A through E show the FFT procedure for the interference waveform $V_I(Z)$. That is, the V(Z) curve shown in FIG. 14A is converted to a linear scale, from which the reference signal curve $V_R(Z)$ is subtracted, providing the interference wavefrom $V_I(Z)$ shown in FIG. 14B. This interference waveform $V_I(Z)$ is sampled at a distance interval $\Delta Zs$, and the scale on the abscissa is converted from distance to time, obtaining data in the time domain (FIG. 14C). As illustrated in FIG. 14D, dummy sample points are added to both sides of n measured sample points to increase the total number N of sample points in the time domain, thereby achieving a sufficiently high frequency resolution $\Delta f = 1/\Delta tN$ with less number of actually measured sample points. The time series sample data shown in FIG. 14D is subjected to fast Fourier transform to obtain a frequency spectrum which has a peak at the frequency fp corresponding to the dip interval $\Delta Z$ of the V(Z) curve, as shown in FIG. 14E. In the case where a plurality of leaky elastic wave modes are involved, peaks of the same number as the modes appear.

A description will be given of our experiment in which optically polished isotropic fuzed quartz ($SiO_2$) plate was used as the sample 23. As the liquid sound field medium 21 water was used, and a leaky elastic surface wave was measured which could exist and propagate on the boundary between the water and the fused quartz sample 23. The experiment was conducted at an ultrasonic frequency of 226.3 MHz, using an ultrasonic line-focus sapphire lens 18 with a 1.0 mm curvature radius. Such V(Z) and $V_I(Z)$ curves as shown in FIGS. 12A and 12D, respectively, were obtained in accordance with the aforementioned measurement procedure, and the $V_I(Z)$ curve shown in FIG. 12D is represented on the common logarithmic scale, as illustrated in FIG. 12E. From the $V_I(Z)$ curve corresponding to FIG. 12D was obtained the dip interval $\Delta Z = 33.1$ μm, from which was computed a leaky elastic surface wave velocity $V_s = 3432$ m/s. Further, an attenuation ATT of 103 dB/mm was measured from the tilting line 53 of the $V_I(Z)$ curve corresponding to FIG. 12E. The normalized attenuation coefficient $\alpha$ was determined to be $3.64 \times 10^{-2}$, using Eqs. (6) and (7) as the attenuation coefficient of the water ($\alpha_\omega/f^2 = 25.3 \times 10^{-17}$ neper $S^2$/cm at 20° C.). In this experiment, since absorption attenuation of the leaky elastic surface wave in a solid and scattering attenuation of the wave on and in the solid are negligibly small as compared with the attenuation of the wave by acoustic loading of the water on the fused quartz, the measured attenuation is considered to correspond to the attenuation $\alpha_s$ by the acoustic loading effect. The following table 1 shows comparison of calculated values with measured ones.

TABLE 1

| Velocity $V_s$ (m/s) | | Normalized attenuation coefficient $\alpha_s$ | |
|---|---|---|---|
| Measured | Calculated | Measured | Calculated |
| 3432 | 3430 | $3.64 \times 10^{-2}$ | $3.82 \times 10^{-2}$ |

The measured values are in good agreement with the calculated values, with differences of less than 0.1% for the velocity and less than 5% for the attenuation coefficient.

Another experiment was conducted in which a (111)-Ge plate was used as the sample 23 and measurement was carried out at an ultrasonic frequency f of 226.3 MHz. The total number of sample points N for the FFT analysis was 8192, the V(Z) curves were sampled at a rate of about 20 points per dip interval $\Delta Z$, and the velocities $V_s$ and the normalized attenuation coefficients $\alpha_s$ were measured for the leaky elastic surface wave and the leaky pseudo-elastic surface wave in the same manner as described previously, with respect to their propagation directions. The measured values are shown as white circles in FIG. 8. In FIG. 8, the curves 53 and 54 show theoretical values of the normalized attenuation coefficients of the leaky elastic surface wave and the leaky pseudo-elastic surface wave, respectively. It is seen that the measured values are in good agreement with the theoretical values.

While in the above the reference signal curve $V_R(Z)$ is obtained first and then it is subtracted from the V(Z) curve to obtain the $V_I(Z)$ curve, it is also possible to obtain the $V_I(Z)$ curve data by providing the V(Z) curve data to a high-pass filter. In this case, there is the possibility of the peaks of the $V_I(Z)$ curve lying somewhat to the low-frequency side. In the case of obtaining the $V_R(Z)$ curve by using a low-pass filter, it is likely that the peaks near the focal point (Z=0) are rounded, resulting in the information of the $V_I(Z)$ curve near the focal point being distorted. Also it is possible to employ, as the reference signal curve $V_R(Z)$, the V(Z) curve measured on such a material (the sample 23) that a leaky elastic wave is not markedly or never excited between it and the liquid acoustic field medium 21. For example, in the case where water is used as the liquid acoustic field medium 21 and the half aperture angle $\theta m$ of the acoustic lens 18 (FIG. 3) is 60°, the effective aperture angle $\theta e$ is 52.953°, and at 20° C., Vl=1483 m/s and $\rho$ (density)=998.2 Kg/$m^2$. Thus, in the case of a material in which the velocity of a longitudinal wave is lower than $V_s = Vl/\sin \theta e = 1858.6$ m/s, the critical angle $\theta c$ (sin $\theta c = V_l/V_s$) becomes larger than the effective aperture angle $\theta e$, and, therefore, no leaky elastic wave is excited. For instance, in the case of lead (Pb), $V_s = 1960$ m/s ($\rho = 11340$ Kg/$m^3$, $Z = 22.4 \times 10^6$), and the leaky elastic wave is not essentially excited. Accordingly, the reference signal curve $V_R(Z)$ can be obtained by measuring the V(Z) curve for lead (Pb) used as a sample. For obtaining the reference signal curve $V_R(Z)$, it is also possible to use vitreous $As_2S_3$ with $V_s = 2600$ m/s ($\rho = 3200$ Kg/$m^3$, $Z = 8.32 \times 10^6$), vitreous $As_2Se_3$ with $V_s = 2250$ m/s ($\rho = 4.64$ Kg/$m^3$, $Z = 0.44$), Te with $V_s = 2.2 \times 10^3$ m/s, Hg with $V_s = 1450$ m/s, polyethylene, polystyrene and so forth. It is also possible to employ selenium or polytetrafluorethylene as the reference sample. It is desirable that these materials be very low in the longitudinal wave velocity and have specific acoustic impedances close to that of the sample 23 to such an extent that, for example, the impedance values are of the same order as that of the latter.

For obtaining the attenuation ATT, it is also possible to employ the results of the FFT analysis of the $V_I(Z)$ curve data. That is, Eq. (6), if represented in the time domain, becomes as follows:

$$V_I(Z) = C \cdot \exp(-\alpha_0 t) \sin(\eta t + \phi) \qquad (8)$$

This waveform $V_I(Z)$ is subjected to FFT analysis. In general, the spectral distribution of a waveform which is attenuated much spreads as compared with the spectral distribution of an attenuation-free waveform. The waveform represented by Eq. (8) is subjected to the FFT analysis, using a square wave window function with a width of $2t_0$. Letting the magnitudes of the spectra at the frequencies $f_p = \eta/2\pi$, which provides maximal value of spectra, and $$f_s = \left(\eta + \frac{\pi}{t_0}\right)/2\pi$$

be represented by $F(\eta)$ and $$F\left(\eta + \frac{\pi}{t_0}\right),$$

respectively, the attenuation coefficient $\alpha_0$ is given as follows:

$$\alpha_0 = \left(\frac{\pi}{t_0}\right) \left|F\left(\eta \pm \frac{\pi}{t_0}\right)\right| / \left\{|F(\eta)|^2 - \left|F\left(\eta \pm \frac{\pi}{t_0}\right)\right|^2\right\}^{\frac{1}{2}} \quad (9)$$

Using the attenuation coefficient $\alpha_0$ and a conversion coefficient $\Delta Z_s/\Delta t \equiv m$ between the space domain Z and the time domain t, $\gamma$ of Eq. (7) can be obtained by Eq. (10) for various values of Z.

$$\alpha_0 Z/m = 2\{\alpha_\omega t(Z) + \gamma \cdot Z \cdot \tan\theta_s\} \quad (10)$$

$$\text{Therefore, } \gamma = \frac{2\alpha_\omega t(Z) + \alpha_0 Z/m}{2Z\tan\theta_s} = \frac{2\alpha_\omega(Z/\cos\theta_s) + \alpha_0 Z/m}{2\tan\theta_s}$$

A calculation is conducted for + or − of ± in the right side of Eq. (9) and the resulting $\alpha_0$ is substituted into Eq. (10) to obtain $\gamma$, which is then substituted into Eq. (7) to obtain the normalized attenuation coefficient $\alpha_s$.

Figure 12F:
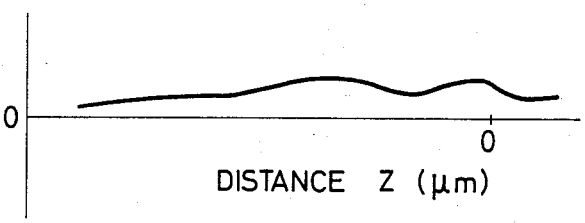
Figure 15:
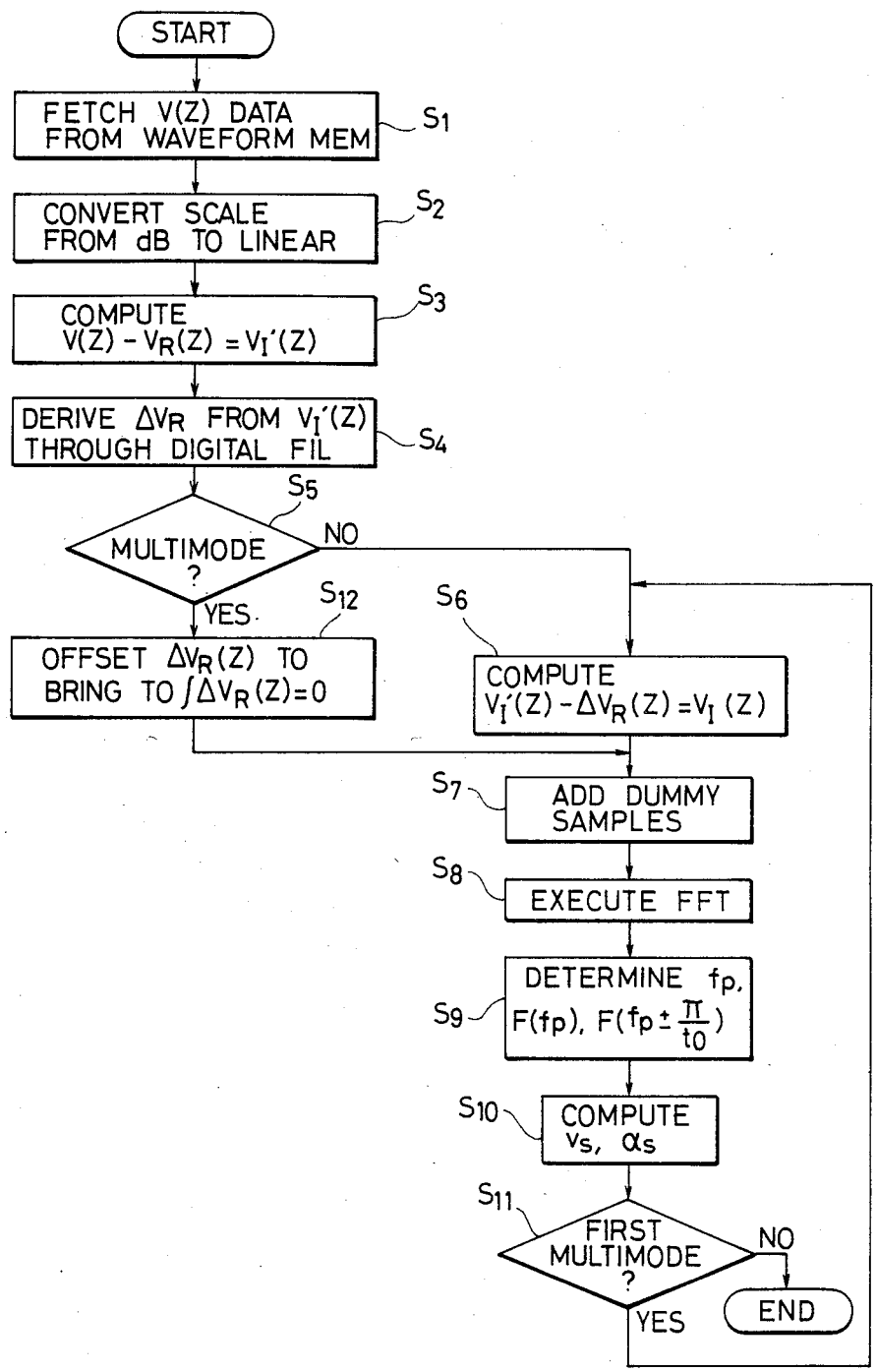
FIG. 15 is a flowchart showing another example of the $V_s$ and $\alpha_s$ measuring operation.

Next, a description will be given, with reference to FIG. 15, of an analysis of the acoustic characteristic through using the above-described method. As described previously in connection with FIG. 7, the V(Z) curve data measured for the sample 23 is prestored in the waveform memory 43. As shown in FIG. 15, when started for processing, the electronic computer 46 reads the V(Z) curve data from the waveform memory 43 in step $S_1$ and, in step $S_2$, converts the V(Z) curve data from the decibel scale to the linear scale to obtain the same V(Z) curve data as shown in FIG. 12B. In step $S_3$ the reference signal curve data $V_R(Z)$ is subtracted from the V(Z) curve data converted to the linear scale, obtaining data $V_I'(Z)$ corresponding to that shown in FIG. 12D. The reference signal curve data $V_R(Z)$ is one that was premeasured for lead (Pb) used as the sample 23 and prestored in the electronic computer 46. In step $S_4$ the data $V_I'(Z)$ is subjected to digital filtering to take out a low-frequency component, obtaining such data $\Delta V_R(Z)$, for example, as shown in FIG. 12F. In step $S_5$ it is decided whether the data is of a multimode or not. This is carried out by reading a mode preset in the electronic computer 46 from the outside prior to the decision. Alternatively, it is checked whether the data $\Delta V_R(Z)$ includes relatively large periodic level variations for Z, and if the level variations exceed a predetermined value, then the data is decided to be of the multimode. When it is decided in step $S_5$ that the data is not of the multimode, $V_I'(Z) - \Delta V_R(Z) = V_I(Z)$ is calculated in step $S_6$. In step $S_7$ dummy sample points are added to the data $V_I(Z)$, as described previously with respect to FIG. 14D, and in step $S_8$ the data is subjected to the FFT analysis. In step $S_9$ the peak frequency $f_p$ of the analyzed spectrum of the $V_I(Z)$ curve, the magnitude $F(f_p)$ of its spectrum and the magnitudes $$F\left(f_p \pm \frac{\pi}{t_0}\right)$$

of the spectrum at frequencies $$\left(f_p \pm \frac{\pi}{t_0}\right)$$

are obtained. In step $S_{10}$ $V_s$ and $\alpha_s$ are calculated using Eqs. (3), (4), (7), (9) and (10). In step $S_{11}$ it is decided whether the calculation is a first one of the multimode, and if not, then the process is finished.

When it is decided that the data is of the multimode, $\Delta V_R(Z)$ obtained in step $S_4$ is integrated in step $S_{12}$ and is offset so that its value may be reduced to zero. Then the process proceeds to step $S_7$, in which dummy sample points are added to the offset data $\Delta V_R(Z)$, after which $V_s$ and $\alpha_s$ are calculated in the same manner as described above. Next, when it is decided in step $S_{11}$ that the calculation in step $S_{10}$ is the first one of the multimode, the process returns to step $S_6$. In this way, $V_s$ and $\alpha_s$ are obtained for the two modes. In the case where a plurality of modes exist as mentioned above, it is preferable to determine the velocity $V_s$ and the attenuation coefficient $\alpha_s$, starting with a leaky elastic wave of higher velocity. When three or more modes of leaky elastic waves exist, the digital filtering in step $S_4$ is repeated, with its cutoff frequency sequentially lowered, until the periodic level variations of the output $\Delta V_R(Z)$ are eliminated. If the level variations are removed by kth filtering, then the output $\Delta V_R(Z)$ obtained by (k−1)th filtering is subjected to the processing in step $S_{12}$ et seq, obtaining $V_s$ and $\alpha_s$ for kth mode. Next, the output $\Delta V_R(Z)$ obtained by the (k−1)th filtering is subtracted from the output $\Delta V_R(Z)$ obtained by (k−2)th filtering, and for the remainder, the processing in step $S_6$ et seq is carried out to obtain $V_s$ and $\alpha_s$ for a (k−1)th mode. Thereafter, similar processing is repeated for each mode.

It is also possible to obtain the velocity $V_s$ and the attenuation $\alpha_s$ solely for the most remarkable one of the modes. As such modes, there are a leaky elastic surface wave, a leaky pseudo-elastic surface wave and a leaky skimming compressional wave, as referred to previously, and they are generically called the leaky elastic wave.

In FIG. 7, by using the transmitter-receiver 16 of the type emitting an ultrasonic line-focus beam and providing a rotating mechanism for turning the sample holder 22 and the transmitter-receiver 16 about the axis (the Z-axis) of the line-focus beam relative to each other, it is possible to obtain the velocity $V_s$ and $\alpha_s$, measuring the V(Z) curve data in the same manner as described above each time the transmitter-receiver 16 are turned through a certain angle relative to each other. The measured values indicated by white circles in FIG. 8 were obtained in this way. The rotational movement, the measurement of the V(Z) curve and the calculations of the velocity $V_s$ and the attenuation coefficient $\alpha_s$ can be performed entirely automatically.

Figure 16:
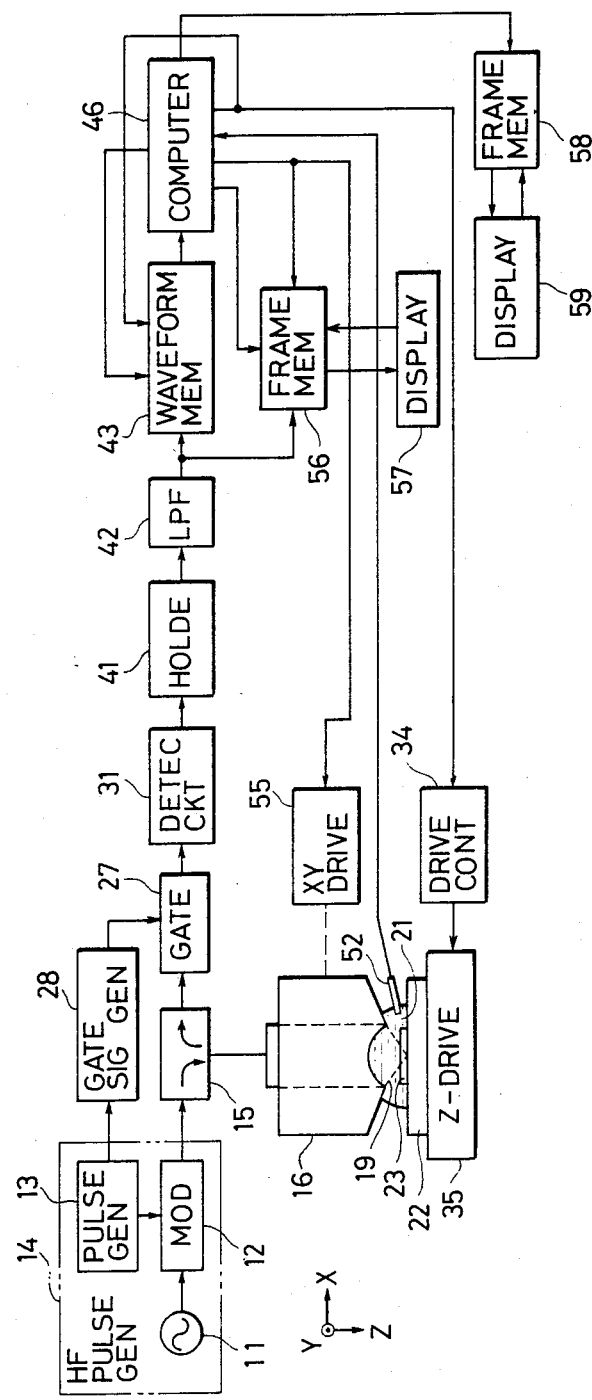
FIG. 16 is a block diagram illustrating an embodiment of the ultrasonic microscope apparatus of the present invention which is equipped with the quantitative measurement function and the imaging measurement function.

Next, a description will be given, with reference to FIG. 16, of a system which has, in combination, the quantitative measuring function of the ultrasonic microscope described in the foregoing and the conventional acoustic imaging measurement function. In FIG. 16, the parts corresponding to those in FIGS. 1 and 7 are identified by the same reference numerals. In this example, the electronic computer 46 performs the aforesaid waveform processing, waveform analysis and calculation of the velocity $V_s$ and the attenuation coefficient $\alpha_s$ and, further, controls the entire system. Accordingly, the Z-axis drive controller 34 responds to a command from the electronic computer 46 to drive the Z-axis driver 35. The V(Z) data obtained during the operation of the driver 35, is input into the waveform memory 43 under the control of the electronic computer 46 too. It is also possible to make such an arrangement that the electronic computer 46 provides only a first start command for the V(Z) measurement to the Z-axis drive controller 34 and the latter operates itself to control driving of the Z-axis driver 35 and store the data into the waveform memory 43.

In this example, since imaging measurement is also performed, the transmitter-receiver 16 is replaced by the type that generates the ultrasonic point-focus beam 19. Furthermore, an XY driver 55 is provided, by which, in this example, the transmitter-receiver 16 can be moved in the X-axis direction perpendicular to the center axis (the Z-axis) of the ultrasonic beam and in a Y-axis direction perpendicular to the X-axis and the Z-axis direction, permitting two-dimensional scanning of the sample 23 by the ultrasonic beam 19. The XY driver 55 is placed under the control of the electronic computer 46, or the electronic computer 46 applies only a start command to the XY driver 55 to cause its controller to control the transmitter-receiver 16 for two-dimensional movement.

The transmitter-receiver 16 is moved two-dimensionally, and at the same time, high-frequency pulses are delivered from the high-frequency pulse generator 14 and ultrasonic pulses are applied to respective points on the sample 23 in the two-dimensional scanning. The reflected waves are received by the transmitter-receiver 16 and amplified and rectified by the detector circuit 31. The reflection signals are each stored as a digital signal in a frame memory 56 at an address corresponding to each two-dimensional scanning point. Upon completion of the two-dimensional scanning of the sample 23, the frame memory 56 is read in synchronism with, for instance, the scanning of a horizontal-vertical scanning type display (for example, a CRT display) 57, and the data thus read out are supplied as display signals to the display 57. In consequence, a spot of the brightness corresponding to the reflected wave level is produced on the screen of the display 57 at the position corresponding to each point of the two-dimensional scanning of the sample 23, providing a display of an ultrasonic microscopic image of the sample 23 on the display screen as a whole.

The velocity distribution can be displayed in the following manner: The V(Z) data is measured for each point of the two-dimensional scanning, then its velocity $V_s$ and attenuation coefficient $\alpha_s$ are calculated, then the velocity $V_s$ is stored in the frame memory 58, and then it is read out in synchronism with the scanning of the display 59 and displayed in a color corresponding to the velocity. Similarly, the attenuation distribution can also be displayed. It is also possible that the V(Z) data is measured only for one or more predetermined representative positions in the two-dimensional scanning, or for one or more positions designated by data input into the electronic computer 46 from the outside, as required, and the velocity $V_s$ and attenuation coefficient $\alpha_s$ are calculated and displayed in color or in the form of numeric values, superimposed on the ultrasonic microscopic image on the display 57, or displayed on another display 59. Alternatively, the contents of the frame memory 56 and the contents of the frame memory 58 may also be displayed on one display 57 alternately with each other. In this way, the structural and acoustic characteristics of each part of the sample 23 can be observed in comparison.

Figure 17:
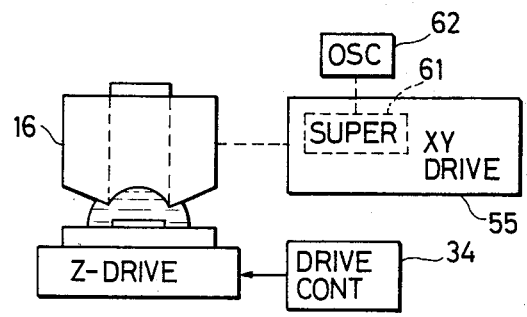
FIG. 17 is a block diagram showing a modification of the apparatus illustrated in FIG. 16.

Also it is possible to divide the two-dimensional scanning region into a plurality of smaller regions, to average, for each region, the velocities $V_s$ and the attenuation coefficients $\alpha_s$ obtained at respective points and to display the mean values. Such averaging processing can also be effected in the following manner: As partly shown in FIG. 17, after moving the transmitter-receiver 16 by the XY driver 55 to a desired position, a small vibration signal is applied to a superimposing part 61 of the XY driver 55 in the X-axis and/or the Y-axis direction from an oscillator 62 and a small vibration of sufficiently higher velocity than the movement in the Z-axis direction is applied to the transmitter-receiver 16, by which is obtained a reflected wave averaged in each segment or small region defined by the amplitude of the vibration, and the V(Z) curve data is also averaged in the segment or small region at each position in the Z-axis direction.

Further, an ultrasonic point-focus transmitter-receiver and an ultrasonic line-focus beam transmitter-receiver may be combined so that they can be switched over from one to the other by such means as, for example, an objective lens switching current employed in an optical microscope. For acoustic imaging measurement only the point-focus beam transmitter-receiver is used, and for quantitative measurement either one of the line-focus beam transmitter-receiver and the point-focus beam transmitter-receiver can be used. In the case of using the line-focus beam, there can be obtained the V(Z) curve data which is an average of the acoustic characteristics at the respective points on the focused beam line in the direction perpendicular thereto. Moreover, by slightly oscillating the line-focus beam in a direction perpendicular to the focused line at a speed sufficiently higher than that of the movement of the sample in the Z-axis direction, it is possible to obtain mean V(Z) curve data for the small region defined by the amplitude of the oscillation and the length of the focused line of the beam. In the case of using the point-focus beam for quantitative measurement, there can be obtained the V(Z) curve data which is an average of the acoustic characteristics at the focused point in all the directions thereabout.

Figure 18:
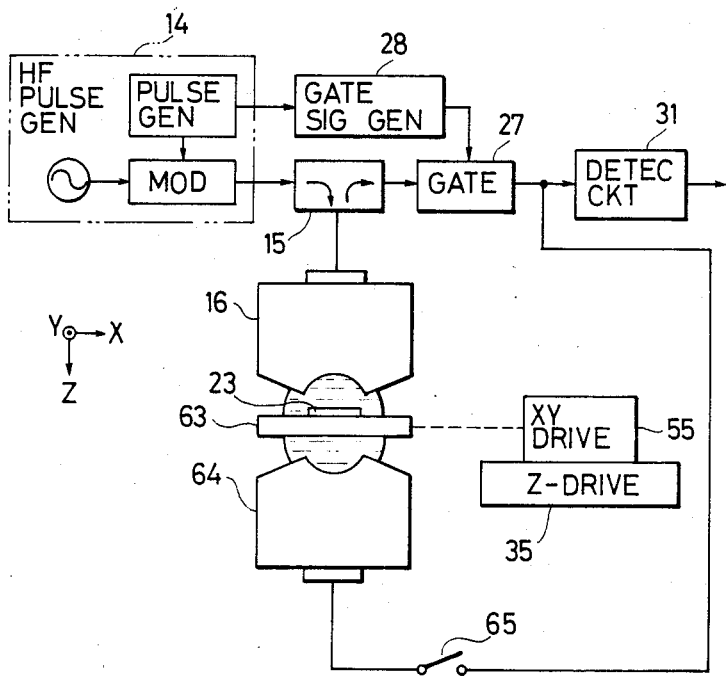
FIG. 18 is a block diagram illustrating a part of an example of an ultrasonic microscope apparatus equipped with a transmission type imaging measurement function.

In the above explained arrangement, it is also possible to provide a receiver 64 which is disposed opposite the transmitter-receiver 16 with respect to the sample 23 as shown in FIG. 18 and has a focal point at the focal point of the transmitter-receiver 16 so that a transmitted wave can be measured instead of a reflected wave. In the case of conducting imaging measurement the transmitter-receiver 16 is changed over to the point-focus type and used as a transmitter. The sample 23 is located at the focal points of the transmitter 16 and the receiver 64. A switch 65 is turned ON and an ultrasonic pulse radiated from the transmitter-receiver 16 is transmitted through the sample 23, the transmitted pulse is received by the receiver 64 and an electric signal of the received output is provided to the detector circuit 31, from which measured data is supplied to the frame memory 56, as described previously in connection with FIG. 16. In this case, the sample holder 63 is moved under the control of the XY driver 55. By the transmitted wave, an ultrasonic microscopic image is obtained on the display 57. During the imaging measurement the gate 27 is held closed by the control of the electronic computer 46; namely, it receives only the electric signal of the transmitted wave from the receiver 64. Further, in the case of conducting the quantitative measurement, either the point-focus beam or the line-focus beam is selected and the switch 65 is turned OFF. The sample holder 63 is moved in the Z-axis direction by the Z-axis driver 35 and, if necessary, in XY directions by the XY driver 55 during the quantitative measurement.

FIG. 19 schematically illustrates an example of the construction of ultrasonic microscope apparatus equipped with the imaging measurement function and the quantitative measurement function. A chassis 67 is mounted on an air-cushion shock absorber (not shown). On the chassis 67 is mounted the Z-axis driver 35, which is adapted so that its moving part 69 is moved up and down by the control of a step motor 68. Mounted on the moving part 69 is a rotary mechanism 71, which is controlled by a controller 72 to turn its rotary part 71a about the Z-axis. By the rotary mechanism 71, the velocity $V_s$ and the attenuation coefficient $\alpha_s$ can be measured for the direction of propagation of a wave. Mounted on the rotary mechanism 71 is a goniometer 73, on which is mounted the sample holder 22, on which, in turn, is disposed the sample 23. The sample 23 is fixedly held, as required, as by means of vacuum suction. On the other hand, an X-axis driver 74 is mounted on the chassis 67 in side-by-side relation to the Z-axis driver 35 and has its moving part 74a adapted to be moved by a step motor 75 along the X-axis. Mounted on the moving part 74a is a Y-axis driver 76, the moving part 76a of which is moved by a step motor (not shown) along the Y-axis. Mounted on the moving part 76a is a goniometer 77, on which a support arm 78 is fixed at one end. The other end portion of the support arm 78 is extended over the sample holder 22, and the transmitter-receiver 16 is attached to the underside of the extended portion of the support arm 78 and is adjusted so that its focal line or focal point may lie in the vicinity of the sample 23. A cable 79 for supplying high-frequency pulses to the transmitter-receiver 16 and for leading out the reflected wave output is fixed at one end to the support arm 78. The goniometers 73 and 77 are to perform such control that during two-dimensional scanning its scanning plane may agree with the surface of the sample 23, or in the case of using the line-focus beam, the focused line of the beam may correctly be parallel to the surface of the sample 23.

Now, a description will be given of our experiments of the imaging measurement and the quantitative measurement conducted on Mn—Zn ferrites with average grain sizes of 8 μm and 50 μm, respectively. The surfaces of the ferrites were polished to such an extent that no significant variations in contrast were observed on the surfaces by an optical microscope. The acoustic images of these samples were observed by using a 440 MHz point-focus beam. For the sample with the average grain size of 50 μm, individual grains 10 to 100 μm in size and their boundaries could be clearly recognized. For the sample with the average grain size of 8 μm, smaller grains down to several μm in size were seen, but the image was blurred. In the quantitative measurement for the samples through using a 226.3 MHz line-focus beam having a focused line of 1 mm length, dips in the V(Z) curve for the sample with the average grain size of 50 μm were appreciably shallow as compared with the dips in the V(Z) curve for the sample with the average grain size of 8 μm. The velocity $V_s$ and the attenuation coefficient $\alpha_s$ for the sample with the average grain size of 8 μm were 3317 m/s and $3.68 \times 10^{-2}$, respectively, and the sample with the average grain size of 50 μm showed a velocity $V_s$ of 3299 m/s and an attenuation coefficient $\alpha_s$ of $5.87 \times 10^{-2}$. The attenuation for the sample with larger grains was greater than that for the sample with the smaller grains.

While in the foregoing the sample holder 22 is moved in the Z-axis direction, the transmitter-receiver 16 may also be moved instead, and the sample holder 22 may also be moved in the X-axis and the Y-axis direction. Further, in the foregoing, the sample 23 is moved towards the transmitter-receiver after the focal point or focal line was brought to the vicinity of the sample, but they may also be moved apart from the state in which they lie close to each other to the state in which the sample 23 lies on the focal point or focal line. The liquid acoustic field medium 21 may be replaced with a high-pressure gas. Although in the foregoing the waveform processing and the waveform analysis are carried out by the electronic computer 46, it is also possible to employ processors or hardware arrangements for the exclusive use for them, respectively. Besides, the waveform analysis may also be effected directly for the V(Z) curve data without involving the waveform processing.

As has been described in the foregoing, according to the ultrasonic microscope system of the present invention, by the waveform analysis of the V(Z) curve data for a sample through the use of the spectral analysis techniques, even if the V(Z) curve contains irregularities, the acoustic characteristics, i.e. the velocity $V_s$ and the attenuation coefficient $\alpha_s$, of leaky elastic waves can correctly be measured. In addition, by the waveform analysis, the both characteristics can be measured from one V(Z) curve at high accuracy for one or each of a plurality of wave propagation modes. Moreover, the provision of the imaging measurement function in combination with the quantitative measurement function permits the detection of, for example, the state of grains of a sample and the corresponding acoustic characteristics thereof.

It will be apparent that many modifications and variations may be effected without departing from the scope of the novel concepts of the present invention.

What is claimed is:

1. An ultrasonic microscope apparatus comprising:
   a high-frequency pulse generator for generating high-frequency pulses obtained by pulse-modulating a carrier of an ultrasonic frequency;
   a duplexer connected to the high-frequency pulse generator, for separating a transmission signal and a reception signal;
   an ultrasonic transmitter-receiver connected to the duplexer and supplied with the high-frequency pulse, for radiating an ultrasonic wave of the ultrasonic frequency as a focused ultrasonic beam and receiving a reflected wave;
   a sample holder for holding a sample for exposure to irradiation by the focused ultrasonic beam from the ultrasonic transmitter-receiver via an acoustic field medium;

Z-axis direction moving means for moving the sample holder and the ultrasonic transmitter-receiver relative to each other along the axis of the ultrasonic beam;

a detector circuit connected to the duplexer, for receiving an electric signal of the reflected wave from the sample received by the ultrasonic transmitter-receiver and amplifying and rectifying the electric signal to provide an electric reflection signal of a level corresponding to the level of the reflected wave; and waveform analyzing means connected to the detecting circuit, for inputting the output reflection signal therefrom upon each occurrence of the relative movement for a fixed distance and analyzing an envelope waveform of a series of input reflection signals by a spectral analysis to obtain the dip interval of interference of a leaky elastic wave and a directly reflected wave from the sample.

2. An ultrasonic microscope apparatus according to claim 1, including waveform processing means for waveform-processing the reflection signal to pick up a leaky elastic wave component, and attenuation calculating means for obtaining the attenuation of the leaky elastic wave component.

3. An ultrasonic microscope apparatus according to claim 1, which includes waveform processing means for waveform-processing the reflection signal to pick up a leaky elastic wave component, and wherein the leaky elastic wave component is analyzed by the waveform analyzing means to obtain the dip interval of the interference.

4. An ultrasonic microscope apparatus according to claim 3, including attenuation calculating means for obtaining the attenuation of the leaky elastic wave component.

5. An ultrasonic microscope apparatus according to claim 4, wherein the waveform processing is to subtract from the reflection signal a reference signal indicating a reference level of the interference of the reflected wave and the leaky elastic wave.

6. An ultrasonic microscope apparatus according to claim 3, wherein the waveform processing is to subtract from the reflection signal a reference signal indicating a reference level of the interference of the reflected wave and the leaky elastic wave.

7. An ultrasonic microscope apparatus according to claim 5 or 6, including low-pass filter means supplied with the reflection signal output to produce the reference signal.

8. An ultrasonic microscope apparatus according to claim 7, wherein the low-pass filter means is a digital filter.

9. An ultrasonic microscope apparatus according to claim 5 or 6, including means for obtaining, as the reference signal, the output envelope waveform of the detecting circuit, using, as the sample, a material for which a leaky elastic wave is not remarkably or never excited between the acoustic field medium and the sample.

10. An ultrasonic microscope apparatus according to claim 9, wherein the sample for obtaining the reference signal is one that has a specific acoustic impedance close to that of the sample for measurement.

11. An ultrasonic microscope apparatus according to claim 9, wherein the sample for obtaining the reference signal is lead.

12. An ultrasonic microscope apparatus according to claim 9, wherein the sample for obtaining the reference signal is selenium.

13. An ultrasonic microscope apparatus according to claim 5 or 6, including means for subjecting the envelope of the output reflection signal of the detecting circuit to fast Fourier transform to obtain a spectrum, removing therefrom a high-frequency component and waveform-synthesizing the remaining low-frequency component to obtain the reference signal.

14. An ultrasonic microscope apparatus according to claim 3 or 4, wherein the waveform processing means is high-pass or band-pass filter supplied with the reflection signal to pick up the leaky elastic wave component.

15. An ultrasonic microscope apparatus according to claim 4, wherein the attenuation calculating means is means for obtaining the attenuation from the gradient of a line joining peaks of the waveform of the leaky elastic wave component.

16. An ultrasonic microscope apparatus according to claim 5, including means for calculating the velocity of the leaky elastic wave component in the sample from the dip interval of the interference, the calculating means comprising means for obtaining the gradient of a line joining peaks of the waveform of the leaky elastic wave component with its level on a logarithmic scale and means for calculating the attenuation through using the gradient, the velocity, the attenuation coefficient of the acoustic field medium, the critical angle of the leaky elastic wave and the ultrasonic frequency used.

17. An ultrasonic microscope apparatus according to claim 5, wherein the attenuation calculating means is means for subjecting the leaky elastic wave component to fast Fourier transform to obtain its spectrum, obtaining its attenuation coefficient from the maximum level of the spectrum and the level of a frequency spaced $1/(2t_0)$ (where $2t_0$ is the width of a square wave window function of the fast Fourier transform) apart from the frequency of the maximum value level and then calculating the attenuation of the leaky elastic wave component from its attenuation coefficient and velocity, the attenuation coefficient of the acoustic field medium, the critical angle of the leaky elastic wave component and the ultrasonic frequency used.

18. An ultrasonic microscope apparatus according to claim 17, wherein the waveform processing means is means for applying to a low-pass filter the remainder $V'_f(Z)$ obtained by subtracting the reference signal from the envelope of the reflection signal and subtracting the output of the low-pass filter from the $V'_f(Z)$ to obtain the leaky elastic wave component.

19. An ultrasonic microscope apparatus according to claim 17 or 18, wherein the waveform processing means includes means for applying to a low-pass filter the remainder $V'_f(Z)$ obtained by subtracting the reference signal from the envelope of the reflection signal, integrating the filter output $\Delta V_R(Z)$ and applying a DC offset to the filter output $\Delta V_R(Z)$ so that it may become zero, wherein the waveform analyzing means includes means for subjecting the DC-offset output $\Delta V_R(Z)$ to obtain its spectrum, and wherein the attenuation calculating means includes means for obtaining the attenuation coefficient of the leaky elastic wave component from the level of the maximum value in the spectrum of the $\Delta V_R(Z)$ and the level of a frequency spaced $1/(2t_0)$ apart from the frequency of the level of the maximum value and then calculating the attenuation of another leaky elastic wave component from the attenuation coefficnet, the velocity of said another leaky elastic wave, the attenuation coefficient of the acoustic field medium, the critical angle of said another leaky elastic wave and the ultrasonic frequency used.

20. An ultrasonic microscope apparatus according to claim 6, wherein the waveform analyzing means is means for subjecting the leaky elastic wave component to fast Fourier transform.

21. An ultrasonic microscope apparatus according to claim 16, wherein the waveform analyzing means is means for subjecting the leaky elastic wave component to fast Fourier transform.

22. An ultrasonic microscope apparatus according to any one of claims 17, 20 and 21, wherein the fast Fourier transform is performed, with dummy sample points disposed before and after the leaky elastic wave component.

23. An ultrasonic microscope apparatus according to any one of claims 1 to 6 and 15 to 18, wherein the ultrasonic transmitter-receiver produces an ultrasonic point-focus beam.

24. An ultrasonic microscope apparatus according to any one of claims 1 to 6 and 15 to 18, wherein the ultrasonic transmitter-receiver produces an ultrasonic line-focus beam.

25. An ultrasonic microscope apparatus according to claim 24, including rotating means for rotating the ultrasonic transmitter-receiver and the sample holder relative to each other about the axis of the ultrasonic beam.

26. An ultrasonic microscope apparatus according to any one of claims 1 to 6 and 15 to 18, including a holding circuit connected to the detector circuit, for holding the level of its output reflection signal, and a waveform memory for storing the output of the holding circuit for each relative movement of the sample holder and the ultrasonic transmitter-receiver for a fixed distance by the Z-axis moving means, the waveform memory being read out for the waveform analysis and/or the waveform processing.

27. An ultrasonic microscope apparatus according to any one of claims 1 to 6 and 15 to 18, including means for measuring the temperature of the acoustic field medium, and means for correcting the velocity in the acoustic field medium.

28. An ultrasonic microscope apparatus according to any one of claims 1 to 6 and 15 to 18, including XY moving means for moving the sample holder and the ultrasonic transmitter-receiver relative to each other in a plane perpendicular to the axis of the ultrasonic beam to scan the sample two-dimensionally, means for receiving a reflected wave or transmitted wave from the sample and converting it into an electric signal, and means for amplifying and rectifying the electric signal, and display means for providing an image display of the magnitude of the level of the amplified-rectified output corresponding to each position of the two-dimensional scanning of the sample.

29. An ultrasonic microscope apparatus according to claim 28, wherein the dip interval of the interference and/or the attenuation are obtained for one or more positions in the two-dimensional scanning of the sample.

30. An ultrasonic microscope apparatus according to claim 28, wherein the ultrasonic transmitter-receiver produces an ultrasonic point-focus beam, and which includes oscillating means for oscillating the ultrasonic transmitter-receiver and the sample holder relative to each other in the plane of the two-dimensional scanning along an axis and/or another axis perpendicular thereto at a speed sufficiently higher than the speed of the movement by the Z-axis moving means.

31. An ultrasonic microscope apparatus according to claim 28, wherein the ultrasonic transmitter-receiver produces an ultrasonic line-focus beam, and which includes oscillating means for oscillating the ultrasonic transmitter-receiver and the sample holder relative to each other in the plane of the two-dimensional scanning in a direction perpendicular to the focused line of the ultrasonic line-focus beam at a speed sufficiently higher than the speed of the movement by the Z-axis moving means.

* * * * *